United States Patent
Camden

(10) Patent No.: US 6,686,391 B2
(45) Date of Patent: *Feb. 3, 2004

(54) N-CHLOROPHENYLCARBAMATE AND N-CHLOROPHENYLTHIOCARBAMATE COMPOSITIONS

(75) Inventor: James Berger Camden, West Chester, OH (US)

(73) Assignee: University of Arizona Foundation, Tucson, AZ (US)

( * ) Notice: Subject to any disclaimer, the term of this patent is extended or adjusted under 35 U.S.C. 154(b) by 12 days.

This patent is subject to a terminal disclaimer.

(21) Appl. No.: 09/748,652

(22) Filed: Dec. 22, 2000

(65) Prior Publication Data

US 2001/0002403 A1 May 31, 2001

Related U.S. Application Data

(60) Continuation of application No. 09/408,664, filed on Jul. 29, 1999, now Pat. No. 6,177,460, which is a continuation-in-part of application No. 09/364,021, filed on Jul. 30, 1999, now Pat. No. 6,251,870, which is a division of application No. 08/876,705, filed on Jun. 16, 1997, now Pat. No. 5,932,609, which is a division of application No. 08/680,468, filed on Jul. 15, 1996, now Pat. No. 5,932,604.
(60) Provisional application No. 60/001,888, filed on Aug. 4, 1995, now abandoned.

(51) Int. Cl.$^7$ ............................................... A61K 31/27
(52) U.S. Cl. ........................................ 514/485; 514/482
(58) Field of Search ................................. 514/485, 488

(56) References Cited

U.S. PATENT DOCUMENTS

| | | |
|---|---|---|
| 2,695,225 A | 11/1954 | Witman |
| 2,734,911 A | 2/1956 | Strain |
| 2,806,051 A | 9/1957 | Brockway |
| 3,799,758 A | 3/1974 | Franz |
| 3,853,530 A | 12/1974 | Franz |
| 3,903,297 A | 9/1975 | Robert |
| 4,408,052 A | 10/1983 | Hozumi |
| 4,501,756 A * | 2/1985 | Kato et al. ............ 514/376 |
| 4,542,219 A | 9/1985 | Hozumi |
| 4,544,512 A | 10/1985 | Hozumi |
| 4,649,203 A | 3/1987 | Nojima |
| 4,775,758 A | 10/1988 | Nojima |
| 4,866,059 A | 9/1989 | Temple |
| 5,114,951 A | 5/1992 | King |
| 5,254,715 A | 10/1993 | Picard et al. |
| 5,336,690 A | 8/1994 | Picard et al. |
| 5,629,341 A | 5/1997 | Camden |
| 5,656,615 A * | 8/1997 | Camden .................. 514/76 |
| 5,665,713 A | 9/1997 | Camden |
| 5,665,751 A | 9/1997 | Camden |
| 5,705,521 A | 1/1998 | Abraham |
| 5,767,138 A | 6/1998 | Camden |
| 5,770,616 A | 6/1998 | Camden |
| 5,840,742 A | 11/1998 | Camden |
| 5,854,231 A | 12/1998 | Camden |
| 5,872,142 A | 2/1999 | Camden |
| 5,880,144 A | 3/1999 | Camden |
| 5,900,429 A | 5/1999 | Camden |
| 5,902,804 A | 5/1999 | Camden |
| 5,908,855 A | 6/1999 | Camden |
| 5,914,341 A | 6/1999 | Dinsmore et al. |
| 5,929,099 A | 7/1999 | Camden |
| 5,932,604 A | 8/1999 | Camden |
| 5,932,609 A | 8/1999 | Camden |
| 6,025,377 A | 2/2000 | Camden |
| 6,060,484 A | 5/2000 | Fritz et al. |
| 6,077,862 A | 6/2000 | Camden |
| 6,090,796 A | 7/2000 | Camden |
| 6,110,953 A | 8/2000 | Camden |
| 6,136,835 A | 10/2000 | Camden |
| 6,177,460 B1 | 1/2001 | Camden |

FOREIGN PATENT DOCUMENTS

| | | |
|---|---|---|
| WO | WO96/2878 | 10/1996 |
| WO | WO 96/32103 | 10/1996 |
| WO | WO 96/32104 | 10/1996 |
| WO | WO 96/32107 | 10/1996 |
| WO | WO 96/32115 | 10/1996 |
| WO | WO 96/40119 | 12/1996 |
| WO | WO 96/40120 | 12/1996 |
| WO | WO 96/40122 | 12/1996 |
| WO | WO 97/05870 | 2/1997 |
| WO | WO 97/05872 | 2/1997 |
| WO | WO 97/05873 | 2/1997 |
| WO | WO 98/32440 | 7/1998 |
| WO | WO 98/51303 | 11/1998 |
| WO | Wo 98/51304 | 11/1998 |
| WO | WO 99/07672 | 2/1999 |
| WO | WO 99/59585 | 11/1999 |

OTHER PUBLICATIONS

Ansel, Ph.D., Preface, Contents, and Index herewith, (1976), Introduction to Pharmaceutical Dosage Forms, Second Edition, Lea & Febiger.

Audus, "General Growth Responses of Plants", pp. 55–82, (1976), Herbicides, 2nd Ed., Vol 1, Academic Press.

Audus, "Toxic Hazards in the Use of Herbicides", pp. 385–387, (1976), Herbicides, 2nd Ed., vol. 1, Academic Press.

Bandurina et al., "Synthese and Antitumor Activity of Aminphosphonic Acids", pp. 35–37, (1978), Pharm. Chem. J., Vol. 12, Plenum Publishing Corporation.

(List continued on next page.)

Primary Examiner—Jerome D. Goldberg
(74) Attorney, Agent, or Firm—Haynes and Boone, LLP

(57) ABSTRACT

Methods for the treatment of cancers or viral infections in mammals are disclosed that include administration of an N-chlorophenylcarbamate, or an N-chlorophenylthiocarbamate, or a salt thereof. Such compounds may be used in combination with a chemotherapeutic agent and/or a potentiator.

2 Claims, No Drawings

OTHER PUBLICATIONS

Brown et al., "Microtubule Biogenesis and Cell Shape in Ochromonas III. Effects of the Herbicidal Mitotic Inhibitor Isopropyl N–Phenylcarbamate on Shape and Flagellum Regeneration.", pp. 514–536, (1974),The Journal of Cell Biology, vol. 61, Rockefeller University Press (with abstract).

Dus et al., "Cytostatic Activity in vitro of Phosphonic Acid Derivatives", pp. 325–329, (1985), Archivum Immunologiae et Therapiae Experimentalis, vol. 33, Polish Academy of Sciences.

Lieberman, et al., Preface, Contents, Contributors, Sunject Index herewith, (1981), Pharmaceutical Dosage Forms, vol. 2, Marcel Dekker, Inc.

Mashkovsky, et al. "Drugs for treating cancer diseases", pp. 1–6, (1993), Medical Agents (A Handbook for physicians) Part II, 12th edition, Meditsina publishers.

Merck Index, 12th ed., "2240—Chloropropham," p. 2241, (1996), Merck & Co., Inc.

Merck Index, 11th ed., "7769—Procodazole," p. 1232, (1989), Merck & Co., Inc.

Mochida et al., "Chemical control of green leafhoppers to prevent virus diseases, especially tungro disease, on susceptible/intermediate rice cultivars in the tropics", pp. 195–208, (1986) Tropical Agriculture Research Series, vol. 19, Ministry of Agriculture et al.

NASR, "Computer Assisted Structure–Anticancer Aactivity Correlations of Carbamates and Thiocarbamates", pp. 831–836, (1985), Journal of Pharmaraceutical Sciences, American Pharmaceutical Association.

Pratt et al. "Other Antagonists of Pyrimidine Metabolism", pp. 86–87, (1994), The Anticancer Drugs, Second Edition, Oxford University Press.

Schuster, "Effects of Herbicides of the Urea and Carbamate Type and Chemicals for Sucker Control on virus–Infected Tabacco Plants", pp. 25–27, (1973), Ber. Inst. Tabakforschung, vol. 20, with English translation (published by American Chemical Society).

Tabibi, et al., "Disperse Systems", pp. 299–394, (1996), Modern Pharmaceutics, Third Edition, Marcel Dekker, Inc.

Wattenburg et al., "Inhibitors of Colon Carcinogenesis", pp. 2432–2435, (1977), Cancer, American Cancer Society, Inc.

Zilkah et al., "Effect of inhibitors of plant cell division on mammalian tumor cells in vitro", pp. 1879–1883, (1981), Cancer Research, American Association for Cancer Research.

Zilkah et al., "1072—Effect of Plant Mitotic Inhibitors on Mammalian Tumor Cells", p. 270, (1981), Proceedings of American Association for Cancer Research, vol. 22, American Association for Cancer Research.

Pending Application of Camden, Ser. No. 09/264,942, filed Mar. 9, 1999. (5638D2C).

Pending Application of Camden, Ser. No. 09/375,173, filed Aug. 16, 1999. (5702CR).

Pending Application of Camden, Ser. No. 09/469,389, filed Dec. 22, 1999. (5703D2C).

Pending Application of Camden, Ser. No. 09/360,499, filed Jul. 26, 1999. (5781D).

Pending Application of Camden, Ser. No. 09/674,182, filed Jul. 16, 1996, CPA filed Feb. 10, 1999. (5782).

Pending Application of Camden, Ser. No. 09/371,457, filed Aug. 10, 1999. (5784R).

Pending Application of Camden, Ser. No. 09/371,459, filed Aug. 10, 1999. (5784R2).

Pending Application of Camden, Ser. No. 09/364,021, filed Jul. 30, 1999. (5785D2).

Pending Application of Camden, Ser. No. 09/312,948, filed May 17, 1999. (5786D).

Pending Application of Camden, Ser. No. 09/394,383, filed Sep. 9, 1999. (5786DR).

Pending Application of Camden, Ser. No. 09/218,884, filed Dec. 22, 1998. (6496D).

Pending Application of Camden, Ser. No. 09/857,811, filed May 16, 1997, CPA filed Jul. 28, 1999. (6643).

Pending Application of Camden, Ser. No. 09/312,949, filed May 17, 1999. (7161R).

Pending Application of Camden, Ser. No. 09/374,717, filed Aug. 13, 1999. (7719).

Pending Application of Camden, Ser. No. 09/462,243, filed Jan. 5, 2000. (6642).

Pending Application of Camden, Ser. No. 09/552,408, filed Apr. 19, 2000. (6496D2).

Pending Application of Camden, Ser. No. 09/552,825, filed Apr. 20, 2000. (6643D2).

Pending Application of Camden, Ser. No. 09/552,820, filed Apr. 20, 2000. (6643D3).

Pending Application of Camden, Ser. No. 09/560,059, filed Apr. 27, 2000. (5781D3).

Pending Application of Camden, Ser. No. 09/603,040, filed Jun. 26, 2000. (5781DC).

Pending Application of Camden, Ser. No. 09/791,986, filed Apr. 28, 2000. (8068).

Pending Application of Camden, Ser. No. 09/562,709, filed Apr. 28, 2000. (8069).

Pending Application of Camden, Ser. No. 09/602,170, filed Jun. 22, 2000. (5783C2).

Pending Application of Camden, Ser. No. 09/603,322, filed Jun. 26, 2000. (5781D2).

Pending Application of Camden, Ser. No. 09/618,990, filed Jul. 18, 2000. (5702CRD).

Pending Application of Camden, Ser. No. 09/639,188, filed Aug. 15, 2000. (5784R2D).

Pending Application of Camden, Ser. No. 09/640,148, filed Aug. 16, 2000. (5784R2C).

Pending Application of Camden, Ser. No. 09/645,708, filed Aug. 24, 2000. (5785D2RD).

Pending Application of Camden, Ser. No. 09/645,427, filed Aug. 24, 2000. (5785D2RD2).

Pending Application of Camden, Ser. No. 09/640,920, filed Aug. 17, 2000. (7161R2).

Pending Application of Camden, Ser. No. 09/640,918, filed Aug. 17, 2000. (1761R3).

Pending Application of Camden, Ser. No. 09/640,919, filed Aug. 17, 2000. (7161R4).

Pending Application of Camden, Ser. No. 09/676,407, filed Sep. 29, 2000. (6643R).

Pending Application of Camden, Ser. No. 09/676,034, filed Sep. 29, 2000. (6643R2).

Pending Application of Camden, Ser. No. 09/676,033, filed Sep. 29, 2000. (6643R3).

Pending Application of Camden, Ser. No. 09/676,409, filed Sep. 29, 2000. (6643R4).

Pending Application of Camden, Ser. No. 09/676,032, filed Sep. 29, 2000. (6643R5).

Pending Application of Camden, Ser. No. 09/676,031, filed Sep. 29, 2000. (6643R6).

Pending Application of Camden, Ser. No. 09/676,030, filed Sep. 29, 2000. (6643R7).

Pending Application of Camden, Ser. No. 09/676,029, filed Sep. 29, 2000. (6643R8).
Pending Application of Camden, Ser. No. 09/676,408, filed Sep. 29, 2000. (6643R9).
Pending Application of Camden, Ser. No. 09/676,202, filed Sep. 29, 2000. (6643R10).
Pending Application of Camden, Ser. No. 09/670,169, filed Sep. 26, 2000. (8250).
Pending Application of Camden, Ser. No. 09/670,168, filed Sep. 26, 2000. (8251).
Pending Application of Camden, Ser. No. 09/670,170, filed Sep. 26, 2000. (8252).
Pending Application of Camden, Ser. No. 09/670,166, filed Sep. 26, 2000. (8253).
Pending Application of Camden, Ser. No. 09/737,835, filed Dec. 15, 2000. (5782C).
Pending Application of Camden, Ser. No. 09/748,651, filed Dec. 22, 2000. (5638D2CD).
Pending Application of Camden, Ser. No. 09/748,652, filed Dec. 22, 2000. (5785D2RC).
Pending Application of Camden, Ser. No. Not Yet Correctly Assigned, fiels Feb. 23, 2001. (5702CRC).

* cited by examiner

N-CHLOROPHENYLCARBAMATE AND N-CHLOROPHENYLTHIOCARBAMATE COMPOSITIONS

This application is a continuation application of copending U.S. Ser. No. 09/408,664, filed Jul. 29, 1999 now U.S. Pat. No. 6,177,460, which is a continuation-in-part application of U.S. Ser. No. 09/364,021, filed Jul. 30, 1999 now U.S. Pat. No. 6,251,870 which is a divisional application of U.S. Ser. No. 08/876,705, filed Jun. 16, 1997, now issued as U.S. Pat. No. 5,932,609, which is a divisional application of Ser. No. 08/680,468, filed Jul. 15, 1996, now issued as U.S. Pat. No. 5,932,604. U.S. Ser. No. 08/680,468 claims priority to U.S. Ser. No. 08/420,913 filed Apr. 12, 1995, now U.S. Pat. No. 5,629,341, and to U.S. Ser. No. 60/001,888, filed Aug. 4, 1995 now abandoned.

TECHNICAL FIELD

The present invention relates to methods for the treatment of cancer or a viral infection in mammals, particularly in human and warm blooded animals, using a composition containing N-chlorophenylcarbamate, N-chlorophenylthiocarbamate or salt thereof. The methods may use such a compound in combination with a potentiator or a chemotherapeutic agent.

BACKGROUND OF THE INVENTION

Cancers are the leading cause of death in animals and humans. The exact cause of cancer is not known, but links between certain activities such as smoking or exposure to carcinogens and the incidence of certain types of cancers and tumors has been shown by a number of researchers.

Many types of chemotherapeutic agents have been shown to be effective against cancers and tumor cells, but not all types of cancers and tumors respond to these agents. Unfortunately, many of these agents also destroy normal cells. The exact mechanism for the action of these chemotherapeutic agents are not always known.

Despite advances in the field of cancer treatment the leading therapies to date are surgery, radiation and chemotherapy. Chemotherapeutic approaches are said to fight cancers that are metastasized or ones that are particularly aggressive. Such cytocidal or cytostatic agents work best on cancers with large growth factors, i.e., ones whose cells are rapidly dividing. To date, hormones, in particular estrogen, progesterone and testosterone, and some antibiotics produced by a variety of microbes, alkylating agents, and anti-metabolites form the bulk of therapies available to oncologists. Ideally cytotoxic agents that have specificity for cancer and tumor cells while not affecting normal cells would be extremely desirable. Unfortunately, none have been found and instead agents that target especially rapidly dividing cells (both tumor and normal) have been used.

Clearly, the development of materials that would target cancer cells due to some unique specificity for them would be a breakthrough. Alternatively, materials that were cytotoxic to cancer cells while exerting mild effects on normal cells would be desirable.

Human Immunodeficiency Virus (HIV), the etiological agent for AIDS (acquired immune deficiency syndrome), is a member of the lentiviruses, a subfamily of retroviruses. HIV integrates its genetic information into the genome of the host. Most importantly, HIV infects and invades cells of the immune system; it breaks down the body's immune system and renders the patient susceptible to opportunistic infections and neoplasms. HIV-1 is cytopathic for T4 lymphocytes, cells of the immune system that express the cell surface differentiation antigen CD4. In addition to CD4+T cells, the host range of HIV includes cells of the mononuclear phagocytic lineage, including blood monocytes, tissue macrophages, Langerhans cells of the skin and dendritic reticulum cells within lymph nodes.

Precursor cells in the bone marrow are released into the blood in an immature circulating form known as monocytes. Monocytes use the blood strictly as a transport medium. Once they arrive where they're going to be used, they leave the blood and complete differentiation into macrophages. Cells of the monocyte/macrophage lineage are a major target population for infection with HIV in the body and are thought to provide reservoirs of virus for disseminating infection throughout the body. HIV is also neurotropic, capable of infecting monocytes and macrophages in the central nervous system causing severe neurologic damage. They can interact and fuse with CD4-bearing T cells, causing T cell depletion and thus contributing to the pathogenesis of AIDS.

Progression from HIV infection to AIDS is primarily determined by the effects of HIV on the cells that it infects, including CD4+T lymphocytes and macrophages. In turn, cell activation, differentiation and proliferation regulate HIV infection and replication in those cells. HIV and other lentiviruses can proliferate in nonproliferating, terminally differentiated macrophages and growth-arrested T lymphocytes. This ability of lentiviruses, including HIV, to replicate in nonproliferating cells, particularly in macrophages, is believed to be unique among retroviruses.

Due to the above-mentioned problems in the art, the present inventor has sought improvements and provides such improvements herein.

SUMMARY OF THE INVENTION

Methods for treatment of mammals, and in particular, warm blooded animals and humans that are affected by cancer or viral infection comprising administering a therapeutically effective amount of an N-chlorophenylcarbamate, an N-chlorophenylthiocarbamate, or a salt thereof, are provided by the present invention. An N-chlorophenylcarbamate, or an N-chlorophenylthiocarbamate has the formula:

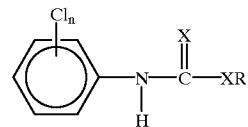

wherein n is from 1 to 3, X is oxygen or sulfur, and R is selected from the group consisting of hydrogen, lower alkyl, lower alkenyl, cyclohexyl, phenalkyl of up to 8 carbon atoms, and phenyl.

These compositions are effective in killing or slowing the growth of cancers, yet are safer than adriamycin on normal, healthy cells. The compositions are also particularly effective against cells of monocytic lineage infected with HIV.

DETAILED DESCRIPTION OF THE INVENTION

A. Definitions

As used herein, "a therapeutically effective amount," means the concentration or quantity or level of the compound of the present invention that can attain a particular medical end, such as control or destruction of cancer cells, virally-infected cells, or viruses without producing unacceptable toxic symptoms. The term "safe and effective amount" refers to the quantity of a component which is sufficient to yield a desired therapeutic response without undue adverse side effects (such as toxicity, irritation, or allergic response) commensurate with a reasonable benefit/risk ratio when used in the manner of this invention. The specific "safe and effective amount" will vary with such factors as the particular condition being treated, the physical condition of the patient, the type of mammal being treated, the duration of the treatment, the nature of concurrent therapy (if any), and the specific formulations employed and the structure of the compounds or its salts.

As used herein, a "subject in need thereof," is a mammal having cancer or having a viral infection. As used herein, "cancer" refers to all types of cancers, or neoplasms or benign or malignant tumors. In one embodiment, those cancers that attack normal healthy blood cells or bone marrow are contemplated by the present invention. Preferred cancers for treatment using methods provided herein include carcinoma. By "carcinoma" is meant a benign or malignant epithelial tumor and includes, but is not limited to, breast carcinoma, prostate carcinoma, non-small cell lung carcinoma, colon carcinoma, CNS carcinoma, melanoma carcinoma, ovarian carcinoma, or renal carcinoma. A preferred host is a human host.

As used herein, "a cell of monocytic lineage" means a cell having a bone marrow precursor cell and that differentiates into a macrophage cell, and includes monocytes and macrophages.

As used herein, "viruses" includes viruses that cause disease in warm blooded animals including retroviruses such as HIV or HTLV, influenza, rhinoviruses, herpes, or the like.

As used herein, an N-chlorophenylcarbamate, or an N-chlorophenylthiocarbamate, or salt thereof are "compounds of the present invention." Such compounds are further set forth in Section B infra.

As used herein, "potentiators" are materials that affect the immune system or enhance the effectiveness of the drugs and are further set forth in section E herein.

As used herein, "chemotherapeutic agents" includes DNA-interactive agents, antimetabolites, tubulin-interactive agents, hormonal agents and others, such as asparaginase or hydroxyurea and are as further set forth in Section D infra.

Following long-standing patent law convention, the terms "a" and "an" mean "one or more" when used in this application, including the claims.

B. N-chlorophenylcarbamate or N-chlorophenylthio carbamate

An N-chlorophenylcarbamate or an N-chlorophenylthiocarbamate has the following structure

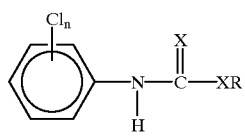

wherein n is from 1 to 3, X is oxygen or sulfur, and R is selected from the group consisting of hydrogen, lower alkyl, lower alkenyl, cyclohexyl, phenalkyl of up to 8 carbon atoms and phenyl.

Preferred compounds are those in which R is alkyl with 1 to 4 carbons, preferably, isopropyl; X is oxygen; n is 1; and the chloro group is in the 3 position on the phenyl group. N-3-chlorophenylcarbamate is a most preferred compound.

These compounds are prepared according to the method described in U.S. Pat. No. 2,695,225 issued to Witman (1954) and U.S. Pat. No. 2,734,911 issued to Strain (1956), incorporated by reference herein. As used herein, a "a compound of the present invention" is an N-chlorophenylcarbamate, or an N-chlorophenylthiocarbamate, or a salt thereof.

Pharmaceutically acceptable addition salts of N-chlorophenylcarbamate, or an N-chlorophenylthiocarbamate, are considered within the scope of compounds of the present invention and are salts with an organic or inorganic acid. Preferred acid addition salts are chlorides, bromides, sulfates, nitrates, phosphates, sulfonates, formates, tartrates, maleates, malates, citrates, benzoates, salicylates, ascorbates, or the like. Such salts may be synthesized from the compound, or derivative thereof, of the present invention that contains a basic or acidic moiety by conventional chemical methods. Generally, such salts may be prepared by reacting a free acid or base form of the compound, or derivative thereof, with a stoichiometric amount of the appropriate base or acid in water or in an organic solvent, or in a mixture of the two; generally, nonaqueous media like ether, ethyl acetate, ethanol, isopropanol, or acetonitrile are preferred. Further suitable salts may be found in *Remington: The Science and Practice of Pharmacy,* 19th ed., Mack Publishing Company, Easton, Pa., 1995, p. 1457.

Pharmaceutically acceptable salts of the compounds of the present invention include conventional non-toxic salts or the quaternary ammonium salts of the compounds or derivatives formed, for example, from non-toxic inorganic or organic acids. For example, such conventional non-toxic salts include those derived from inorganic acids such as hydrochloric, hydrobromic, sulfuric, sulfamic, phosphoric, nitric, or the like; and salts prepared from organic acids such as acetic, propionic, succinic, glycolic, stearic, lactic, malic, tartaric, citric, ascorbic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, or the like. Preferred acid addition salts are chlorides, bromides, sulfates, nitrates, phosphates, sulfonates, formates, tartrates, maleates, malates, citrates, benzoates, salicylates, ascorbates, or the like.

Further, included within the scope of the compound, or salts thereof, useful for the present invention are prodrugs. As used herein, a "prodrug" is a drug covalently bonded to a carrier wherein release of the drug occurs in vivo when the prodrug is administered to a mammalian subject. Prodrugs of the compounds of the present invention are prepared by modifying functional groups present in the compounds in such a way that the modifications are cleaved, either in routine manipulation or in vivo, to yield the desired compound. Prodrugs include compounds wherein hydroxy, amine, or sulfhydryl groups are bonded to any group that, when administered to a mammalian subject, is cleaved to form a free hydroxyl, amino, or sulfhydryl group, respectively. Examples of prodrugs include, but are not limited to, acetate, formate, or benzoate derivatives of alcohol or amine functional groups in the compounds of the present invention; phosphate esters, dimethylglycine esters, aminoalkylbenzyl esters, aminoalkyl esters or carboxyalkyl esters of alcohol or phenol functional groups in the compounds of the present invention; or the like.

Compounds of the present invention are known for their herbicidal activities. They are systemic herbicides used to prevent and eradicate certain plants or weeds. Systemic herbicides are differentiated from other herbicides by their ability to be absorbed by the plant and to move through the plant. This systemic ability is not a necessary requirement of the compounds of this invention.

C. Screening Assays

Screening assays for determining those cancers susceptible to treatment using compounds of the present invention include incubating cell line models representing specific cancers as set forth, for example, by the National Cancer Institute, in the presence and absence of such compounds. Viability of cells may be determined by the MTT assay (Promega Corp., Madison, Wis. 53711), or the SRB (sulforhodamine B) assay (Skehan, et al., *JNCI,* 82:13, 1107, 1990). Susceptibility to said compounds exists when viability in the presence of a compound of the present invention is less than viability in the absence of such compound.

Exemplary cell line models representing specific cancers include, but are not limited to, the following:

Non-small cell lung cancer: NCIH23, NCIH324, NCIH522, A549/ATCC, A549(ASC), CALU1, EKVX, NCIH125M, NCIH226, NCIH520, SKMES1, NCIH322M, NCIH358M, NCIH460, NCIH292, HOP62, HOP18, HOP19, HOP92, LXFL 529, SW1573, LXFS 650L, ML1019, ML1076, ML1045, or UABLG22;

Small cell lung cancer. NCIH69, NCIH146, NCIH82, NCIH524, DMS 114, DMS 273, HOP27, SHP77, or RHOS;

Colon cancer: HT29, HCC2998, HCT116, LOVO, SW1116, SW620, COLO 205, DLD1, WIDR, COLO 320DM, HCT15, CXF 280, KM12, KM20L2, COLO 741, CXF 264L, COLO 746, UABC02, ML1059, CAC02, HT29/PAR, HT29/MDR1, or NB4;

Breast cancer: MCF7, MCF7/ADRRES, ZR751, ZR7530, MDAMB231/ATCC, HS 578T, UISOBCA1, MCF7/ATCC, SKBR3, MDAMB435, MDAN, BT549, T47D, MDAMB231, MAXF 401, BT474, or MDAMB468;

Ovarian cancer: OVCAR3, OVCAR4, OVCAR5, OVCAR8, A2780, IGROV1, SKOV3, OVXF 899, A1336, or ES2;

Leukemia: P388, P3888/ADR, CCRFCEM, CCRFSB, K562, MOLT4, L1210, HL60(TB), RPMI8226, SR, or K562/ADR;

Fibroblast: IMR90, or CCD19LU;

Renal cancer: UO31, SN12C, SN12S1, SN12K1, SN12L1, SN12A1, A498, A704, CAKI1, RXF 393, RXF631, 7860, SW156, TK164, 769P, SS78, ACHN, TK10, RXF 486L, UOK57, or UOK57LN;

Melanoma: LOX IMVI, MALME3M, RPMI7951, SKMEL2, SKMEL5, SKMEL28, SKMEL31, UCSD 242L, UCSD 354L, M14, M19MEL, UACC62, UACC257, MEXF 514L, or UABMEL3;

Prostate cancer: PC3, PC3M, DU145, LNCAP, 1013L, UMSCP1, WIS, JE, RER, MRM, DHM, AG, RB, RVP, FC, WAE, DB/SMC, JCA1, ND1, WMF, TSUPRI, JECA, GDP, T10, WBW, RVP1, or WLL;

CNS cancer: SNB7, SNB19, SNB44, SNB56, SNB75, SNB78, U251, TE671, SF268, SF295, SF539, XF 498, SW 1088, SW 1783, U87 MG, SF767, SF763, A172, or SMSKCNY;

Bone/muscle: A204/ATCC, OHS, TE85, A673, CHA59, MHM 25, RH18, RH30, or RD; and

Lymphoma: AS283, HT, KD488, PA682, SUDHL7, RL, DB, SUDHL1, SUDHL4, SUDHL10, NUDUL1, or HUT 102.

D. Chemotherapeutic Agents

Chemotherapeutic agents are generally grouped as DNA-interactive agents, antimetabolites, tubulin-interactive agents, hormonal agents, other agents such as asparaginase or hydroxyurea, and agents as set forth in Table 1. Each of the groups of chemotherapeutic agents can be further divided by type of activity or compound. Chemotherapeutic agents used in combination with an N-chlorophenylcarbamate, or an N-chlorophenylthiocarbamate, or salts thereof of the present invention may be selected from any of these groups but are not limited thereto. For a detailed discussion of the chemotherapeutic agents and their method of administration, see Dorr, et al, *Cancer Chemotherapy Handbook,* 2d edition, pages 15–34, Appleton & Lange (Connecticut, 1994) herein incorporated by reference.

DNA-interactive agents include alkylating agents, e.g. cisplatin, cyclophosphamide, altretamine; DNA strand-breakage agents, such as bleomycin; intercalating topoisomerase II inhibitors, e.g., dactinomycin and doxorubicin); nonintercalating topoisomerase II inhibitors such as, etoposide and teniposde; and the DNA minor groove binder picamydin, for example.

The alkylating agents form covalent chemical adducts with cellular DNA, RNA, or protein molecules, or with smaller amino acids, glutathione, or similar chemicals. Generally, alkylating agents react with a nucleophilic atom in a cellular constituent, such as an amino, carboxyl, phosphate, or sulfhydryl group in nucleic acids, proteins, amino acids, or in glutathione. The mechanism and the role of these alkylating agents in cancer therapy is not well understood.

Typical alkylating agents include, but are not limited to, nitrogen mustards, such as chlorambucil, cyclophosphamide, isofamide, mechlorethamine, melphalan, uracil mustard; aziridine such as thiotepa; methanesulphonate esters such as busulfan; nitroso ureas, such as carmustine, lomustine, streptozocin; platinum complexes, such as cisplatin, carboplatin; bioreductive alkylator, such as mitomycin, and procarbazine, dacarbazine and altretamine.

DNA strand breaking agents include bleomycin, for example.

DNA topoisomerase II inhibitors include the following intercalators, such as amsacrine, dactinomycin, daunorubicin, doxorubicin (adriamycin), idarubicin, and mitoxantrone; nonintercalators, such as etoposide and teniposide, for example.

A DNA minor groove binder is plicamycin, for example.

Antimetabolites interfere with the production of nucleic acids by one of two major mechanisms. Certain drugs inhibit production of deoxyribonucleoside triphosphates that are the immediate precursors for DNA synthesis, thus inhibiting DNA replication. Certain of the compounds are analogues of purines or pyrimidines and are incorporated in anabolic nucleotide pathways. These analogues are then substituted into DNA or RNA instead of their normal counterparts.

Antimetabolites useful herein include, but are not limited to, folate antagonists such as methotrexate and trimetrexate; pyrimidine antagonists, such as fluorouracil, fluorodeoxyuridine, CB3717, azacitidine, cytarabine, and floxuridine; purine antagonists include mercaptopurine, 6-thioguanine, fludarabine, pentostatin; sugar modified analogs include cyctrabine, fludarabine; and ribonucleotide reductase inhibitors include hydroxyurea.

Tubulin interactive agents act by binding to specific sites on tubulin, a protein that polymerizes to form cellular microtubules. Microtubules are critical cell structure units. When the interactive agents bind the protein, the cell can not form microtubules Tubulin interactive agents include vincristine and vinblastine, both alkaloids and paclitaxel, for example.

Hormonal agents are also useful in the treatment of cancers and tumors. They are used in hormonally susceptible tumors and are usually derived from natural sources. Hormonal agents include, but are not limited to, estrogens, conjugated estrogens and ethinyl estradiol and diethylstilbesterol, chlortrianisen and idenestrol; progestins such as hydroxyprogesterone caproate, medroxyprogesterone, and megestrol; and androgens such as testosterone, testosterone propionate; fluoxymesterone, and methyltestosterone.

Adrenal corticosteroids are derived from natural adrenal cortisol or hydrocortisone. They are used because of their anti-inflammatory benefits as well as the ability of some to inhibit mitotic divisions and to halt DNA synthesis. These compounds include, but are not limited to, prednisone, dexamethasone, methylprednisolone, and prednisolone.

Leutinizing hormone releasing hormone agents or gonadotropin-releasing hormone antagonists are used primarily the treatment of prostate cancer. These include leuprolide acetate and goserelin acetate. They prevent the biosynthesis of steroids in the testes.

Antihormonal antigens include, for example, antiestrogenic agents such as tamoxifen, antiandrogen agents such as flutamide; and antiadrenal agents such as mitotane and aminoglutethimide.

Further agents include the following: hydroxyurea appears to act primarily through inhibition of the enzyme ribonucleotide reductase, and asparaginase is an enzyme which converts asparagine to nonfunctional aspartic acid and thus blocks protein synthesis in the tumor.

Taxol (paclitaxel) is a preferred chemotherapeutic agent.

A listing of currently available chemotherapeutic agents according to class, and including diseases for which the agents are indicated, is provided as Table 1.

TABLE 1

Neoplastic Diseases[1] for which Exemplary Chemotherapeutic agents are Indicated

| Class | Type of Agent | Name | Disease[2] |
|---|---|---|---|
| Alkylating Agents | Nitrogen Mustards | Mechlorethamine (HN$_2$) | Hodgkin's disease, non-Hodgkin's lymphomas |
| | | Cyclophosphamide Ifosfamide | Acute and chronic lymphocytic leukemias, Hodgkin's disease, non-Hodgkin's lymphomas, multiple myeloma, neuroblastoma, breast, ovary, lung, Wilms' tumor, cervix, testis, soft-tissue sarcomas |
| | | Melphalan | Multiple myeloma, breast, ovary |
| | | Chlorambucil | Chronic lymphocytic leukemia, primary macroglobulinemia, Hodgkin's disease, non-Hodgkin's lymphomas |
| | | Estramustine | Prostate |
| | Ethylenimines and Methylmelamines | Hexamethylmelamine | Ovary |
| | | Thiotepa | Bladder, breast, ovary |
| | Alkyl Sulfonates | Busulfan | Chronic granulocytic leukemia |
| | Nitrosoureas | Carmustine | Hodgkin's disease, non-Hodgkin's lymphomas, primary brain tumors, multiple myeloma, malignant melanoma |

TABLE 1-continued

Neoplastic Diseases[1] for which Exemplary Chemotherapeutic agents are Indicated

| Class | Type of Agent | Name | Disease[2] |
|---|---|---|---|
| | | Lomustine | Hodgkin's disease, non-Hodgkin's lymphomas, primary brain tumors, small-cell lung |
| | | Semustine | Primary brain tumors, stomach, colon |
| | | Streptozocin | Malignant pancreatic insulinoma, malignant carcinoid |
| | Triazenes | Dacarbazine Procarbazine Aziridine | Malignant melanoma, Hodgkin's disease, soft-tissue sarcomas |
| Antimetabolites | Folic Acid Analogs | Methotrexate Trimetrexate | Acute lymphocytic leukemia, choriocarcinoma, mycosis fungoides, breast, head and neck, lung, osteogenic sarcoma |
| | Pyrimidine Analogs | Fluorouracil Floxuridine | Breast, colon, stomach, pancreas, ovary, head and neck, urinary bladder, premalignant skin lesions (topical) |
| | | Cytarabine Azacitidine | Acute granulocytic and acute lymphocytic leukemias |
| | Purine Analogs and Related Inhibitors | Mercaptopurine | Acute lymphocytic, acute granulocytic, and chronic granulocytic leukemias |
| | | Thioguanine | Acute granulocytic, acute lymphocytic, and chronic granulocytic leukemias |
| | | Pentostatin | Hairy cell leukemia, mycosis fungoides, chronic lymphocytic leukemia |
| | | Fludarabine | Chronic lymphocytic leukemia, Hodgkin's and non Hodgkin's lymphomas, mycosis fungoides |
| Natural Products | Vinca Alkaloids | Vinblastine (VLB) | Hodgkin's disease, non-Hodgkin's lymphomas, breast, testis |
| | | Vincristine | Acute lymphocytic leukemia, neuroblastoma, Wilms' tumor, rhabdomyosarcoma, Hodgkin's disease, non-Hodgkin's lymphomas, small-cell lung |
| | | Vindesine | Vinca-resistant acute lymphocytic leukemia, chronic myelocytic leukemia, melanoma, lymphomas, breast |
| | Epipodophyllotoxins | Etoposide Teniposide | Testis, small-cell lung and other lung, breast, Hodgkin's disease, non-Hodgkin's lymphomas, acute granulocytic leukemia, Kaposi's sarcoma |
| | Antibiotics | Dactinomycin | Choriocarcinoma, Wilms' tumor, rhabdomyosarcoma, testis, Kaposi's sarcoma |
| | | Daunorubicin | Acute granulocytic and acute lymphocytic leukemias |

TABLE 1-continued

Neoplastic Diseases[1] for which Exemplary Chemotherapeutic agents are Indicated

| Class | Type of Agent | Name | Disease[2] |
|---|---|---|---|
| | | Doxorubicin 4'-Deoxy-doxorubicin | Soft-tissue, osteogenic and other sarcomas; Hodgkin's disease, non-Hodgkin's lymphomas, acute leukemias, breast, genitourinary, thyroid, lung, stomach, neuroblastoma |
| | | Bleomycin | Testis, head and neck, skin, esophagus, lung, and genitourinary tract; Hodgkin's disease, non-Hodgkin's lymphomas |
| | | Plicamycin | Testis, malignant hypercalcemia |
| | | Mitomycin | Stomach, cervix, colon, breast, pancreas, bladder, head and neck |
| | Enzymes | L-Asparaginase | Acute lymphocytic leukemia |
| | Taxanes Taxoids | Docetaxel Paclitaxel | Breast, ovarian |
| | Biological Response Modifiers | Interferon Alfa | Hairy cell leukemia, Kaposi's sarcoma, melanoma, carcinoid, renal cell, ovary, bladder, non-Hodgkin's lymphomas, mycosis fungoides, multiple myeloma, chronic granulocytic leukemia |
| | | Tumor Necrosis Factor | Investigational |
| | | Tumor-Infiltrating Lymphocytes | Investigational |
| Miscellaneous Agents | Platinum Coordination Complexes | Cisplatin Carboplatin | Testis, ovary, bladder, head and neck, lung, thyroid, cervix, endometrium, neuroblastoma, osteogenic sarcoma |
| | Anthracenedione | Mitoxantrone | Acute granulocytic leukemia, breast |
| | Substituted Urea | Hydroxyurea | Chronic granulocytic leukemia, polycythemia vera, essential thrombocytosis, malignant melanoma |
| | Methyl Hydrazine Derivative | Procarbazine | Hodgkin's disease |
| | Adrenocortical Suppressant | Mitotane Aminoglutethimide | Adrenal cortex Breast |
| Hormones and Antagonists | Adrenocorticosteroids | Prednisone | Acute and chronic lymphocytic leukemias, non-Hodgkin's lymphomas, Hodgkin's disease, breast |
| | Progestins | Hydroxyprogesterone caproate Medroxyprogesterone acetate Megestrol acetate | Endometrium, breast |
| | Estrogens | Diethylstilbestrol Ethinyl estradiol | Breast, prostate |
| | Antiestrogen | Tamoxifen | Breast |
| | Androgens | Testosterone propionate Fluoxymesterone | Breast |
| | Antiandrogen | Flutamide | Prostate |
| | Gonadotropin-releasing hormone analog | Leuprolide Goserelin | Prostate, Estrogen-receptor-positive breast |

[1]Adapted from Calabresi, P., and B. A. Chabner, "Chemotherapy of Neoplastic Diseases" Section XII, pp 1202–1263 in: Goodman and Gilman's The Pharmacological Basis of Therapeutics, Eighth ed., 1990 Pergamin Press, Inc.; and Barrows, L. R., "Antineoplastic and Immunoactive Drugs", Chapter 75, pp 1236–1262, in: Remington: The Science and Practice of Pharmacy, Mack Publishing Co. Easton, PA, 1995.; both referencesare incorporated by reference herein, in particular for treatment protocols.
[2]Neoplasms are carcinomas unless otherwise indicated.

E. Potentiators

A "potentiator," as used herein, is a material that improves or increases the efficacy of N-chlorophenylcarbamate, or an N-chlorophenylthiocarbamate or a salt thereof, or that acts on the immune system as an immunomodulator, and is used in combination with a compound of the present invention. A potentiator may be an antiviral agent. One such potentiator is triprolidine or its cis-isomer. Triprolidine is described in U.S. Pat. No. 5,114,951 (1992, the patent is incorporated by reference herein). A further potentiator is procodazole, (also named 1H-benzimidazole-2-propanoic acid, or β-(2-benzimidazole) propionic acid or 2-(2-carboxyethyl) benzimidazole or propazol). Procodazole is a non-specific immunoprotective agent active against viral and bacterial infections and may be used in combination with the compounds set forth herein. Procodazole is effective with an N-chlorophenylcarbamate, or an N-chlorophenylthiocarbamate or salt thereof, alone in treating cancers, tumors, leukemia or viral infections, or combined with a chemotherapeutic agent.

Further potentiators include, but are not limited to, propionic acid, salts thereof, or esters thereof; antioxidant vitamins such as vitamins A, C, E, or beta-carotene; abacavir; AL-721 (lipid mixture); amprenavir; Amphotericin B methyl ester, Ampligen (mismatched RNA); anti-AIDS anti-body; anti-human interferon-áantibody; anti-AIDS antibody, ascorbic acid and derivatives thereof; AS-101 (heavy metal based immunostimulant); azidothymidine; â-interferon; Bropirimine; butylated hydroxytoluene; Ciamexon, Cimetidine; CL-246,738, colony stimulating factors, including GM-CSF; Creme Pharmatex (benzalkonium chloride); CS-82 (5-unsubstituted derivative of Zidovudine); Cyclosporin; D-penicillamine (3-mercapto-D-valine); delavirdine; dextran sulphate; dinitrochlorobenzene; efavirenz; erythropoietin; Foscamet (trisodium phosphonoformate); fusidic acid; ganciclovir; glucan; glycyrrhizin, HPA-23 (ammonium-21-tungsto-9-antimonate); human immunevirus antiviral; hyperimmune gamma-globulin, IMREG-1, IMREG-2; indinavir; interferoná; interferon-gamma; interleukin-1 or interleukin-2; isoprinosine; Krestin; LC-9018; lamivudine; lentilart; LF-1695; methionine-enkephalin; Minophagen C; muramyl tripeptide; naltrexone; nelfinavir; Neutropin; nevirapine; Nonoxinol; Omidyl (eflomithine); non-nucleoside inhibitors of reverse transcriptase; nucleoside analogues (ddA, ddC, ddl, ddT, ddG, AZT, and the like); pentamidine isethionate; Phenytoin; polymannoacetate; Peptide T (octapeptide sequence); protease inhibitors; Ribavirin; Rifabutin (ansamycin); ritonavir; RNA immunomodulator; rsT4 (recombinant soluble T4); saquinavir, shosaikoto and ginseng; SK-818 (gernanium-derived antiviral); sodium diethylthiocarbarmate; stavudine; stearic acid derivative; suramin and analogues thereof; thymic humoral factor, TP-5; Thymosin fraction 5 and Thymosin 1; Thymostimulin; TNF (tumor necrosis factor), vitamin B preparations; Trimetrexate; UA001; á-interferon or acyclovir, for example.

A compound, or salt thereof, of the present invention may be combined with a potentiator and with a chemotherapeutic agent in the methods of the present invention.

F. Dosage

Any suitable dosage may be administered in the methods of the present invention. The compound or salt thereof chosen for a particular application, the carrier and the amount will vary widely depending on the species of the warm blooded animal or human, the type of cancer, or the particular viral infection being treated, and depending upon the effective inhibitory concentrations observed in trial studies. The dosage administered will, of course, vary depending upon known factors, such as the pharmacodynamic characteristics of the particular compound, salt, or combination and its mode and route of administration; the age, health, or weight of the subject; the nature and extent of symptoms; the metabolic characteristics of the drug and patient, the kind of concurrent treatment; the frequency of treatment; or the effect desired.

Generally a dosage of as little as about 1–2 milligram (mg) per kilogram (kg) of body weight is suitable, but preferably as little as 10 mg/kg and up to about 10,000 mg/kg may be used. Preferably, a dosage from 15 mg/kg to about 5000 mg/kg is used. Most preferably, the dose is between 150 mg/kg to about 1000 mg/kg. Doses useful in the treatment of cancer or viral infections are 250 mg/kg, 500 mg/kg, 800 mg/kg, 1000 mg/kg, 1500 mg/kg, 2500 mg/kg, 3500 mg/kg, 4000 mg/kg, 5000 mg/kg, or 6000 mg/kg. Any range of doses can be used. Generally, a compound, salt thereof or combination of the present invention can be administered on a daily basis one or more times a day, or one to four times a week either in a single dose or separate doses during the day. Twice weekly dosing over a period of at least several weeks is preferred, and often dosing will be continued over extended periods of time and possible for the lifetime of the patient. However, the dosage and the dosage regimen will vary depending on the ability of the patient to sustain the desired and effective plasma levels of the compounds of the present invention, or salt thereof, in the blood.

The compound, salt thereof, or combination, may be micronized or powdered so that it is more easily dispersed and solubilized by the body. Processes for grinding or pulverizing drugs are well known in the art. For example, a hammer mill or similar milling device can be used. The preferred particle size is less than about $100\mu$ and preferably less than $50\mu$.

Intravenously, the most preferred doses may range from about 1 to about 10 mg/kg/minute during a constant rate infusion.

The dosage for humans is generally less than that used in mice and is typically about $\frac{1}{12}$ of the dose that is effective in mice. Thus, if 500 mg/kg was effective in mice, a dose of 42 mg/kg would be used in humans. For a 60 kg man, this dose would be 2520 mg.

The compounds and salts thereof of the present invention are generally safe. The $LD_{50}$ is high, about 1500 mg/kg given orally in mice and there are no special handling requirements. The compounds can be given orally, and since they are not very soluble, they are preferably given in tablet form or as a suspension.

The compounds and salts thereof of the present invention may be administered in a unit dosage form which may be prepared by any methods known to one of skill in the art in light of the present disclosure. Unit dosages may include from 1 milligram to 1000 milligrams of active ingredient. Preferably the dosage unit will contain from about 10 mg to about 500 mg active ingredient. The active ingredient is generally present in an amount of about 0.5% to about 95% by weight based on the total weight of the dosage unit.

For intravenous use, preferred dosages may range from about 1 to about 10 mg/kg/minute during a constant rate infusion.

A dosage unit may comprise a single compound, or mixtures thereof, with other compounds or other cancer- or viral-inhibiting compounds. The dosage unit may comprise diluents, extenders, carriers, liposomes, or the like. The unit may be in solid or gel form such as pills, tablets, capsules and the like or in liquid form suitable for oral, rectal, topical, intravenous injection or parenteral administration or injection into or around the treatment site. The range and ratio of N-chlorophenylcarbamate, or an N-chlorophenylthiocarbamate, or salt thereof, to chemotherapeutic agent or to potentiator will depend on the type of cancer or viral infection being treated and the particular chemotherapeutic agent or potentiator.

G. Formulations

Formulations of the present invention include the compound of the present invention, N-chlorophenylcarbamate, or an N-chlorophenylthiocarbamate, or salt thereof and, optionally, a chemotherapeutic agent and, optimally, a potentiator generally mixed with a pharmaceutically acceptable carrier. A "pharmaceutical carrier" is a pharmaceutically acceptable solvent, suspending agent or vehicle for delivering a compound of the present invention to the animal or human. The carrier may be liquid or solid and is selected with the planned manner of administration in mind. A "pharmaceutically acceptable" component is one that is suitable for use with humans and/or animals without undue adverse side effects (such as toxicity, irritation, and allergic response) commensurate with a reasonable benefit/risk ratio.

Oral formulations suitable for use in the practice of the present invention include capsules, gels, cachets, tablets, effervescent or non-effervescent powders or tablets, powders or granules; as a solution or suspension in aqueous or non-aqueous liquid; or as an oil-in-water liquid emulsion or a water-in-oil emulsion. The compounds of the present invention may also be presented as a bolus, electuary, or paste.

Generally, formulations are prepared by uniformly mixing the active ingredient with liquid carriers or finely divided solid carriers or both, and then if necessary shaping the product. A pharmaceutical carrier is selected on the basis of the chosen route of administration and standard pharmaceutical practice. Each carrier must be "acceptable" in the sense of being compatible with the other ingredients of the formulation and not injurious to the subject. This carrier can be a solid or liquid and the type is generally chosen based on the type of administration being used. Examples of suitable solid carriers include lactose, sucrose, gelatin, agar and bulk powders. Examples of suitable liquid carriers include water, pharmaceutically acceptable fats and oils, alcohols or other organic solvents, including esters, emulsions, syrups or elixirs, suspensions, solutions and/or suspensions, and solution and or suspensions reconstituted from non-effervescent granules and effervescent preparations reconstituted from effervescent granules. Such liquid carriers may contain, for example, suitable solvents, preservatives, emulsifying agents, suspending agents, diluents, sweeteners, thickeners, and melting agents. Preferred carriers are edible oils, for example, corn or canola oils. Polyethylene glycols, e.g. PEG, are also preferred carriers.

The formulations for oral administration may comprise a non-toxic, pharmaceutically acceptable, inert carrier such as lactose, starch, sucrose, glucose, methyl cellulose, magnesium stearate, dicalcium phosphate, calcium sulfate, mannitol, sorbitol, cyclodextrin, cyclodextrin derivatives, or the like.

Capsule or tablets can be easily formulated and can be made easy to swallow or chew. Tablets may contain suitable carriers, binders, lubricants, diluents, disintegrating agents, coloring agents, flavoring agents, flow-inducing agents, or melting agents. A tablet may be made by compression or molding, optionally with one or more additional ingredients. Compressed tables may be prepared by compressing the active ingredient in a free flowing form (e.g., powder, granules) optionally mixed with a binder (e.g., gelatin, hydroxypropylmethylcellulose), lubricant, inert diluent, preservative, disintegrant (e.g., sodium starch glycolate, cross-linked carboxymethyl cellulose) surface-active or dispersing agent. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, or the like. Lubricants used in these dosage forms include sodium oleate, sodium stearate, magnesium stearate, sodium benzoate, sodium acetate, sodium chloride, or the like. Disintegrators include, for example, starch, methyl cellulose, agar, bentonite, xanthan gum, or the like. Molded tablets may be made by molding in a suitable machine a mixture of the powdered active ingredient moistened with an inert liquid diluent.

The tablets may optionally be coated or scored and may be formulated so as to provide slow- or controlled-release of the active ingredient. Tablets may also optionally be provided with an enteric coating to provide release in parts of the gut other than the stomach.

Exemplary pharmaceutically acceptable carriers and excipients that may be used to formulate oral dosage forms of the present invention are described in U.S. Pat. No. 3,903,297 to Robert, issued Sep. 2, 1975, incorporated by reference herein. Techniques and compositions for making dosage forms useful in the present invention are described in the following references: 7 *Modem Pharmaceutics,* Chapters 9 and 10 (Banker & Rhodes, Editors, 1979); Lieberman et al., *Pharmaceutical Dosage Forms: Tablets* (1981); and Ansel, *Introduction to Pharmaceutical Dosage Forms* 2nd Edition (1976).

Formulations suitable for topical administration in the mouth wherein the active ingredient is dissolved or suspended in a suitable carrier include lozenges which may comprise the active ingredient in a flavored carrier, usually sucrose and acacia or tragacanth; gelatin, glycerin, or sucrose and acacia; and mouthwashes comprising the active ingredient in a suitable liquid carrier.

Topical applications for administration according to the method of the present invention include ointments, cream, suspensions, lotions, powder, solutions, pastes, gels, spray, aerosol or oil. Alternately, a formulation may comprise a transdermal patch or dressing such as a bandage impregnated with an active ingredient and optionally one or more carriers or diluents. To be administered in the form of a transdermal delivery system, the dosage administration will, of course, be continuous rather than intermittent throughout the dosage regimen.

The topical formulations may desirably include a compound that enhances absorption or penetration of the active ingredient through the skin or other affected areas. Examples of such dermal penetration enhancers include dimethylsulfoxide and related analogues.

The oil phase of an emulsion used to treat subjects in the present invention may be constituted from ingredients known to one of skill in the art in light of the present disclosure. An emulsion may comprise one or more emulsifiers. For example, an oily phase may comprise at least one emulsifier with a fat or an oil, with both a fat and an oil, or a hydrophilic emulsifier may be included together with a lipophilic emulsifier that acts as a stabilizer. Together, the emulsifier(s), with or without stabilizer(s), make up an emulsifying wax, and the wax together with the oil and/or fat make up the emulsifying ointment base that forms the oily dispersed phase of the cream formulations.

Emulsifiers and emulsion stabilizers suitable for use in the formulation include Tween 60, Span 80, cetosteryl alcohol, myristyl alcohol, glyceryl monostearate and sodium lauryl sulphate, paraffin, straight or branched chain, mono-or dibasic alkyl esters, mineral oil. The choice of suitable oils or fats for the formulation is based on achieving the desired cosmetic properties, the properties required and compatibility with the active ingredient.

Compounds of the present invention may also be administered vaginally, for example, as pessaries, tampons, creams, gels, pastes, foams or spray formulations containing appropriate carriers in addition to the active ingredient. Such carriers are known in the art in light of the present disclosure.

Formulations for rectal administration may be presented as a suppository with a suitable base comprising, for example, cocoa butter or a salicylate.

Formulations suitable for nasal administration may be administered in a liquid form, for example, nasal spray, nasal drops, or by aerosol administration by nebulizer, including aqueous or oily solutions of the active ingredient. Formulations for nasal administration, wherein the carrier is a solid, include a coarse powder having a particle size, for example, of less than about 100 microns, preferably less than about 50 microns, which is administered in the manner in which snuff is taken, i.e., by rapid inhalation through the nasal passage from a container of the powder held close up to the nose.

Formulations suitable for parenteral administration include aqueous and non-aqueous formulations isotonic with the blood of the intended recipient; and aqueous and non-aqueous sterile suspensions which may include suspending systems designed to target the compound to blood components or one or more organs. The formulations may be presented in unit-dose or multi-dose sealed containers, for example, ampoules or vials. Extemporaneous injections solutions and suspensions may be prepared from sterile powders, granules and tablets of the kind previously described. Parenteral and intravenous forms may also include minerals and other materials to make them compatible with the type of injection or delivery system chosen.

In general, water, a suitable oil, saline, aqueous dextrose (glucose), or related sugar solutions and glycols such as propylene glycol or polyethylene glycols are suitable carriers for parenteral solutions. Solutions for parenteral administration preferably contain a water soluble salt of the active ingredient, suitable stabilizing agents and, if necessary, buffer substances. Antioxidizing agents, such as sodium bisulfite, sodium sulfite, or ascorbic acid, either alone or combined, are suitable stabilizing agents. Also used are citric acid salts thereof, or sodium EDTA. In addition, parenteral solutions may contain preservatives, such as benzalkonium chloride, methyl- or propyl-paraben, or chlorobutanol. Suitable pharmaceutical carriers are described in Remington, cited supra.

The present invention additionally contemplates administering compounds of the herein described invention for use in the form of veterinary formulations, which may be prepared, for example, by methods that are conventional in the art in light of the present disclosure.

Useful pharmaceutical dosage formulations for administration of the compounds of the present invention are illustrated as follows:

Capsules: A large number of unit capsules are prepared by filling standard two-piece hard gelatin capsules each with 100 milligrams of powdered active ingredient, 150 milligrams of lactose, 50 milligrams of cellulose, and 6 milligrams magnesium stearate.

Soft Gelatin Capsules: A mixture of active ingredient in a digestible oil such as soybean oil, cottonseed oil or olive oil is prepared and injected by means of a positive displacement pump into gelatin to form soft gelatin capsules containing 100 milligrams of the active ingredient. The capsules are washed and dried.

Tablets: A large number of tablets are prepared by conventional procedures so that the dosage unit was 100 milligrams of active ingredient, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings can be applied to increase palatability or delay absorption.

Injectable: A parenteral composition suitable for administration by injection is prepared by stirring 1.5% by weight of active ingredient in 10% by volume propylene glycol and water. The solution is made isotonic with sodium chloride and sterilized.

Suspension: An aqueous suspension is prepared for oral administration so that each 5 ml contains 100 mg of finely divided active ingredient, 200 mg of sodium carboxymethyl cellulose, 5 mg of sodium benzoate, 1.0 g of sorbitol solution, U.S.P., and 0.025 ml of vanillin.

Compounds of the present invention may be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

Compounds of the present invention may be coupled with soluble polymers as targetable drug carriers. Such polymers can include polyvinylpyrrolidone, pyran copolymer, polyhydroxylpropylmethacrylamide-phenol, polyhydroxyethylaspartamidephenol, or polyethyleneoxide-polylysine substituted with palmitoyl residues. Furthermore, the compounds of the present invention can be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

H. Method of Treatment

The method of treatment can be any suitable method which is effective in the treatment of the particular cancer or viral infection that is being treated. Treatment includes administering a therapeutically effective amount of the compounds of the present invention in a form described herein above, to a subject in need of treatment.

Compounds of the present invention can be administered by any means that produces contact of the active agent with the agent's site of action in the body, for example, suitable means including, but not limited to, oral, rectal, nasal, topical (including transdermal, aerosol, buccal or sublingual), vaginal, parenteral (including subcutaneous, intramuscular, intravenous or intradermal), intravesical, or injection into or around the cancer or site of viral infection. They can be administered by any conventional means available for use in conjunction with pharmaceuticals, either as individual therapeutic agents or in a combination of therapeutics. Preferably, compounds of the present invention are administered as a pharmaceutical formulation comprising at least one compound of the present invention, as defined above, together with one or more pharmaceutically acceptable carriers. It can be co-administered in the form of a tablet or capsule, as an agglomerated powder or in a liquid form or as a liposome.

The preferred route will vary with the condition and age of the recipient, virus or cancer being treated nature of the disorder, or severity of disorder. It is believed that oral administration, or parenteral treatment is the preferred method of administering the compounds to subjects in need thereof.

In each of the above-described methods, the administering may be in vivo, or may be ex vivo. In vivo treatment is useful for treating diseases in a mammal, preferably the mammal is a human; and ex vivo treatment is useful for purging body fluids, such as blood, plasma, bone marrow, and the like, for return to the body. The nation's blood supply is currently tested for antibodies to HIV. However, the test is still imperfect and samples that yield negative tests can still contain HIV virus. Treating blood and blood products with the compounds of the present invention can add an extra margin of safety to kill any retrovirus that may have gone undetected. Body tissue may be internal or external to an animal body, or, for example, may be the surface skin of the animal.

I. Combination Therapy

Compounds of the present invention may additionally be combined with chemotherapeutic agents, or potentiators, to provide a combination therapy. Combination therapy is intended to include any chemically compatible combination of a compound of the present invention with other compounds of the present invention or other compounds outside of the present invention, as long as the combination does not eliminate the activity of the compound of the present invention. For example, one or more compounds may be combined with a potentiator, or a chemotherapeutic agent. In the case of retroviral infection, a combination therapy with nucleoside analogues such as AZT, nonnucleoside reversal transcriptase inhibitors, TC-3 or protease inhibitors is contemplated by the present invention. In the case of hepatitis, cyclovir, famciclovir or valacyclovir, Ribavirin, interferon or combinations of Ribavirin and interferon or beta globulin is contemplated as a combination therapy. For herpes, a recombinant alpha interferon can be used as a combination therapy. The active agent can be coadministered, for example, in the form of a tablet or capsule, liposome, as an agglomerated powder or in a liquid form. The amount of chemotherapeutic agent or potentiator used can be lower than that of the N-chlorophenylcarbamate or N-chlorophenylthiocarbamate, and can range from 0.5 mg/kg body weight to about 400 mg/kg body weight.

Combination therapy can be sequential, that is the treatment with one agent first and then the second agent, or it can be treatment with both agents at the same time. The sequential therapy can be within a reasonable time after the completion of the first therapy before beginning the second therapy. The treatment with both agents at the same time can be in the same daily dose or in separate doses. For example treatment with one agent on day 1 and the other on day 2. The exact regimen will depend on the disorder being treated, the severity of the disorder and the response to the treatment.

In addition to the use of chemotherapeutic agents and potentiators, an N-chlorophenylcarbamate, or an N-chlorophenylthiocarbamate or a salt thereof can be combined with a fungicide, or an herbicide. Preferred herbicides and fungicides include carbendazim, fluoconazole, benomyl, glyphosate and propicodazole.

J. Pharmaceutical Kits

The present invention also includes pharmaceutical kits useful, for the treatment of cancer or viral infection, that comprise one or more containers containing a pharmaceutical composition comprising a therapeutically effective amount of a compound of the present invention. Such kits can further include, if desired, one or more of various conventional pharmaceutical kit components, such as, for example, containers with one or more pharmaceutically acceptable carriers, additional containers, etc., as will be readily apparent to those skilled in the art. Printed instructions, either as inserts or as labels, indicating quantities of the components to be administered, guidelines for administration, and/or guidelines for mixing the components, can also be included in the kit.

K. Studies

The following studies were performed to test the effectiveness of (3-chlorophenyl)carbamic acid 1-methylethyl ester, Chloropropham™, against certain cancers and viral infections.

HIV Chronic Study

In this model, Chloropropham showed 79% suppression of HIV replication in monocytes. The positive control, interferon, showed 80% suppression. There was 101% increase in HIV replication in T-cells compared to 60% suppression for interferon. AZT showed no action in this model suggesting that the target for inhibition is not reverse transcriptase.

Chronic HIV-1 infected promonocytic cells U1 were derived from an acute HIV-1 infection of the promonocytic cell line, U937. The chronic HIV-1 infected T-cells, ACH-2, were derived from an acute HIV-1 infection of the T cell line, A3.01.

These cells were cultured in medium and the phorbol ester, PMA. PMA causes the cells (both U1 and ACH-2) to be activated and not divide but it also causes the U-1 cells to differentiate. This results in fewer cells in the PMA-treated cultures than the media alone cultures. Cell viability was measured when these cell lines were treated with the test compounds.

Both cell lines constituitively produce a small amount of HIV-1. ACH-2 cell lines tend to produce more HIV-1 than U1 cells as shown by p-24 ELISA. When either cell line is cultured in the presence of PMA there is an increase in the quantity of HIV-1 produced as measured by the p-24 antigen ELISA.

In addition, the number of institute positive HIV mRNA expressing cells per microscopic field is measured. Comparisons can be made from these numbers since the same number of cells were adhered to the glass slides for each drug concentration ($10 \times 10^6$ cells/ml).

The data show that HIV replication in monocytes is inhibited by Chloropropham, thereby, teaching that one activity of Chloropropham is the suppression of HIV replication in monocytes and in related cells. These results demonstrate that Chloropropham can provide a means of immune defense against HIV by suppressing replication in monocytes/macrophage and other cells of monocytic lineage.

Acute HIV Study

In an in vitro acute model for HIV chloropropham inhibited viral replication by 47% at 10 µg/ml and AZT inhibited viral replication by 98% at 1 µg/ml. The therapeutic index for chloropropham is 2.5 compared to 12,500 for AZT. The therapeutic index is ratio of toxic dose of the drug to the efficacious dose of the drug.

While Chloropropham has ability to suppress HIV replication in chronically infected monocytes, the effects are also observed in the setting of an acute infection as demonstrated herein. This suggests that chloropropham has activity at an early stage of HIV replication as well as in the latter stages.

The chronically HIV-1 infected T cell line, ACH-2, and the chronically HIV-1 infected monocytic cell line, U1 are useful in predicting if the compounds could induce virus expression in vivo when given to an individual who is latently infected with HIV and not actively expressing virus. The compounds can inhibit virus replication during an acute HIV-1 infection, and they can also suppress HIV-1 expression from chronically infected monocytes.

Blocking activation of latent virus in chronically infected cells such as macrophages, offers a new addition to the currently available set of anti-retroviral drug mechanisms.

In Vivo Herpes

In an in vivo herpes screening test, at a dose of 150 mg/kg dose, 60% of the mice survived with a 10.2 mean death date. The positive control was acyclovir at 75 mg/kg dose; 60% of the mice survived with a mean death date of 17.2 days.

In Vitro Human Tumor Colony Forming Units Test

Solid tumors removed from patients are minced into 2 to 5 mm fragments and immediately placed in McCoy's Medium 5A plus 10% heat inactivated newborn calf serum plus 1% penicillin/streptomycin. Within 4 hours, these solids tumors are mechanically disassociated with scissors, forced through No. 100 stainless steel mesh, through 25 gauge needles, and then washed with McCoy's medium as described above. Ascitic, pleural, pericardial fluids and bone marrow are obtained by standard techniques. The fluid or marrow is placed in sterile containers containing 10 units of preservative free heparin per ml. of malignant fluid or marrow. After centrifugation at 150×g for 10 minutes, the cells are harvested and washed with McCoy's medium plus 10% heat inactivated calf serum. The viability of cell suspensions is determined on a hemocytometer with trypan blue.

Cells to be cloned are suspended in 0.3% agar in enriched CMRL1066 supplemented with 15% heat inactivated horse serum, penicillin (100 units/ml), streptomycin (2 mg/ml), glutamine (2 mM), insulin (3 units/ml), asparagine (0.6 mg/ml), and HEPES buffer (2 mM). For the continuous exposure test each compound is added to the above mixture. Cells are placed in 35 mm petri dishes in a top layer of agar over an underlayer of agar to prevent growth of fibroblasts. Three plates are prepared for each data point. The plates are placed in a 37° C. incubator, and are removed on day 14 for counting of the number of colonies in each plate. The number of colonies (defined as 50 cells) formed in the 3 compound treated plates is compared to the number of colonies formed in the 3 control plates, and the percent colonies surviving at the concentration of compound can be tabulated. Three positive control plates are used to determine survival rates. Orthosodium vanadate at 200 µg/ml is used as the positive control. If there is <30% colonies in the positive control when compared to the untreated control, the test is evaluated.

At a concentration of 100 µg/ml in a continuous exposure test, chloropropham was effective (%) against breast, colon, non-small cell lung and ovarian tumors. At concentrations of 1 and 10.0 µg/ml chloropropham was not effective.

The human tumor cloning system provided by this study is known by those of skill in the art as providing in vitro predictive assays for selecting an appropriate anticancer agent for an individual patient's cancer.

Colon, Breast and Lung Tumor Cells Test

The following cell culture tests were performed to test the toxicity of N-chlorophenylcarbamates and N-chlorophenylthiocarbamates compounds on colon, breast and lung human tumor cells. The viability of the cells were tested by looking at MTT (3-[4,5-dimethylthiazol-2-yl]-2,5-diphenyltetrazolium bromide) reduction. MTT assay is a well known measure of cell viability.

The colon tumor cells (HT29 from American Type Culture Collection (ATCC)) and the breast cells (MX1 from cell lines from ATCC) were cultured in Eagle's Minimal Essential Medium with 10% fetal bovine serum. The lung tumor cells (A549 from ATCC cell lines) were cultured in Ham's F12 medium with 10% fetal bovine serum.

The tumor cells were passaged and seeded into culture flasks at the desired cell densities. The culture medium was decanted and the cell sheets were washed twice with phosphate buffered saline (PBS). The cells were trypsinized and triturated prior to seeding the flasks. Unless otherwise indicated the cultures were incubated at 37±1° C. in a humidified atmosphere of 5±1% carbon dioxide in air. The cultures were incubated until they were 50–80% confluent.

The cells were subcultured when the flasks were subconfluent. The medium was aspirated from the flasks and the cell sheets rinsed twice with PBS. Next, the Trypsin Solution was added to each flask to cover the cell sheet. The Trypsin Solution was removed after 30–60 seconds and the flasks were incubated at room temperature for two to six minutes. When 90% of the cells became dislodged, growth medium was added. The cells were removed by trituration and transferred to a sterile centrifuge tube. The concentration of cells in the suspension was determined, and an appropriate dilution was made to obtain a density of 5000 cells/ml. The cells were subcultured into the designated wells of the 96-well bioassay plates (200 microliter cell suspension per well). PBS was added to all the remaining wells to maintain humidity. The plates were then incubated overnight before test article treatment.

Each dose of test article was tested by treating quadruplicate wells of cultures with 100 microliter of each dilution. Those wells designated as solvent controls received an additional 100 microliters of methanol control; negative controls wells received an additional 100 microliters of treatment medium. PBS was added to the remaining wells not treated with test article or medium. The plates were then incubated for approximately 5 days.

At the end of the 5 day incubation, each dose group was examined microsopically to assess toxicity. A 0.5 mg/ml dilution of MTT was made in treatment medium, and the dilution was filtered through a 0.45 micrometer filter to remove undissolved crystals. The medium was decanted from the wells of the bioassay plates. Immediately thereafter, 2000 microliter of the filtered MTT solution was added to all test wells except for the two untreated blank test wells. The two blank wells received 200 microliters of treatment medium. The plates were returned to the incubator for about 3 hours. After incubation, the MTT containing medium was decanted. Excess medium was added to each well and the plates were shaken at room temperature for about 2 hours.

The absorbance at 550 nm ($OD_{550}$) of each well was measured with a Molecular Devices (Menlo Park, Calif.) VMax plate reader.

The mean $OD_{550}$ of the solvent control wells and that of each test article dilution, and that of each of the blank wells and the positive control were calculated. The mean OD550 of the blank wells was subtracted from the mean of the solvent control wells, and test article wells, respectively to give the corresponding mean $OD_{550}$.

% of Control=corrected mean $OD_{550}$ of Test Article Dilution×100 corrected mean of $OD_{550}$ of Solvent Control

Dose response curves were prepared as semi-log plots with % of control on the ordinate (linear) and the test article concentration on the abscissa (logarithmic). The $EC_{50}$ was interpolated from the plots for each test article.

For the test articles administered in methanol, separate responses were prepared to correct for the methanol data.

Adriamycin was used as a positive control. In all cases, it was more toxic than any of the test materials by one or two logs. Adriamycin is one of the more potent agents in current use and one with significant side effects. The peak plasma concentration of other, quite effective chemotherapeutic agents may be 10 to 50 times higher than that of Adriamycin. The EC-50 is the concentration at which one half the cells are killed.

TABLE 2

| Test Material | EC-50 Result (ppm or microgram/ml) | | | | | |
|---|---|---|---|---|---|---|
| | HT29 | HT29 | MX1 | MX1 | A549 | A549 |
| Adriamycin | 0.003 | 0.006 | 0.02 | 0.001 | 0.03 | 0.009 |
| Chloroprofam ® | 13.3 | 11.4 | 91.8 | 108 | 12.6 | 92.5 |

In normal healthy cells, the following results were obtained:

TABLE 3

| Test Material | EC-50 | | | | | |
|---|---|---|---|---|---|---|
| | Broncheal Cells | | Kerotinoyle Cells | | Fibroblasts | |
| Chloroprofam ® | 0.002 | >15.2 | 3.9 | 13.0 | >152 | 64.2 |
| Adriamycin | 0.015 | 0.0020 | 0.0035 | 0.0093 | 0.065 | 0.10 |

These studies show that these compositions are effective in killing tumor cells without significantly affecting healthy cells.

Other Cancer Screening Tests

In an in vivo mouse model for breast cancer (MXI), chloropropham showed no activity. In an in vivo mouse model for leukemia (P388), chloropropham showed no activity. In an in vivo mouse model for murine melanoma (B16), chloropropham showed no activity.

The National Cancer Institute tested this material in 1958, 1959, and 1972 and showed no activity at doses from 50–400 mg/kg.

Other Viral Screening Tests

In both an in vivo and an in vitro model for influenza, chloropropham did not show activity. Nor was it active in the screening models for in vitro herpes or in vivo Rhinovirus screening tests.

Methods disclosed and claimed herein can be made and executed without undue experimentation in light of the present disclosure. While the methods of this invention have been described in terms of preferred embodiments, it will be apparent to those of skill in the art that variations may be applied to the composition, methods and in the steps or in the sequence of steps of the method described herein without departing from the concept, spirit and scope of the invention. Such similar substitutes and modifications apparent to those skilled in the art are deemed to be within the spirit, scope and concept of the invention as defined by the appended claims.

What is claimed is:

1. A pharmaceutical composition comprising:

a pharmaceutical carrier selected from the group consisting of lactose, sucrose, starch, glucose, methyl cellulose, cellulose, glycerin, magnesium stearate, silicon dioxide, dicalcium phosphate, calcium sulfate, mannitol, sorbitol, cyclodextrin, cyclodextrin derivative, gelatin, agar, a pharmaceutically acceptable fat, a pharmaceutically acceptable oil, a corn sweetener, a natural guru, a synthetic gum, a glycol, a soluble polymer, a biodegradable polymer, and a liposome; and a therapeutically effective amount of an N-chlorophenylthiocarbamate of the formula:

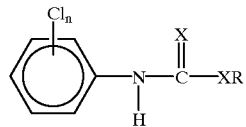

wherein n is from 1 to 3,

X is sulfur; and

R is selected from the group consisting of hydrogen, lower alkyl, lower alkenyl, cyclohexyl, phenalkyl of up to 8 carbon atoms, and phenyl, or a salt thereof.

2. A pharmaceutical composition comprising:

a therapeutically effective amount of an N-chlorophenylthiocarbamate of the formula:

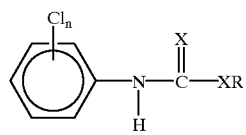

wherein n is from 1 to 3,

S is sulfur; and

R is selected from the group consisting of hydrogen, lower alkyl, lower alkenyl, cyclohexyl, phenalkyl of up to 8 carbon atoms, and phenyl, or a salt thereof, the composition in micronized form.

* * * * *

UNITED STATES PATENT AND TRADEMARK OFFICE
CERTIFICATE OF CORRECTION

PATENT NO. : 6,686,391 B2
DATED : February 3, 2004
INVENTOR(S) : James Berger Camden It is certified that error appears in the above-identified patent and that said Letters Patent is hereby corrected as shown below:

Column 21,
Line 38, delete "guru" and insert therefor, -- gum --;

Column 22,
Line 32, delete "S" and insert therefor; -- X --.

Signed and Sealed this

Sixth Day of April, 2004

JON W. DUDAS
*Acting Director of the United States Patent and Trademark Office*